United States Patent [19]

Dixon

[11] 4,091,046

[45] May 23, 1978

[54] PRODUCTION OF ISOPRENE FROM ISOBUTANE

[75] Inventor: Rolland E. Dixon, Bartlesville, Okla.

[73] Assignee: Phillips Petroleum Company, Bartlesville, Okla.

[21] Appl. No.: 700,686

[22] Filed: Jun. 28, 1976

[51] Int. Cl.$^2$ ............................................. C07C 11/12
[52] U.S. Cl. ........................... 260/680 R; 260/683 D; 260/683.2
[58] Field of Search ............ 260/680 R, 683.2, 683 D, 260/684.15 R

[56] References Cited

U.S. PATENT DOCUMENTS

| | | | |
|---|---|---|---|
| 2,808,499 | 10/1957 | Pitzer et al. | 260/680 R |
| 2,816,150 | 12/1957 | Hepp | 260/680 R |
| 2,848,522 | 8/1958 | Gilmore | 260/680 R |
| 2,873,301 | 2/1959 | Keith | 260/680 R |
| 2,959,293 | 11/1951 | Hall | 260/680 R |
| 2,985,696 | 5/1961 | Magness | 260/680 R |
| 3,409,682 | 11/1968 | Mitsche | 260/683.65 |
| 3,507,931 | 4/1970 | Morris et al. | 260/683.65 |
| 3,527,837 | 9/1970 | Woerner et al. | 260/680 R |
| 3,565,969 | 2/1971 | Hutto et al. | 260/680 R |
| 3,590,096 | 6/1971 | Banks | 260/683 D |
| 3,728,415 | 4/1973 | Arganbright | 260/683.15 R |
| 3,751,514 | 8/1973 | Hoppstock et al. | 260/680 R |
| 3,943,186 | 3/1976 | Nakatoni et al. | 260/683.15 R |

Primary Examiner—O. R. Vertiz
Assistant Examiner—Eugene T. Wheelock

[57] ABSTRACT

Isoamylene is produced from isobutane by cracking isobutane, separating a propylene stream and an isobutylene stream from the cracked product, disproportionating the propylene and isobutylene and separating an isoamylene stream from the disproportionated stream. The isoamylene can be converted into isoprene by dehydrogenation. The isobutane can be produced from normal butane by skeletal isomerization. The ethylene produced during the disproportionation can be dimerized and the butylenes obtained can be either reintroduced into the disproportionation reaction or can be dehydrogenated to butadiene. Isobutane removed from the cracked product, as well as isobutane removed from the disproportionated stream, is recycled into the cracking reaction. Hydrogen produced during the cracking reaction can be used either in the isomerization step for converting normal butane to isobutane, or can be used for hydrogenation of acetylenes produced during the conversion of the normal butene to butadiene.

5 Claims, 1 Drawing Figure

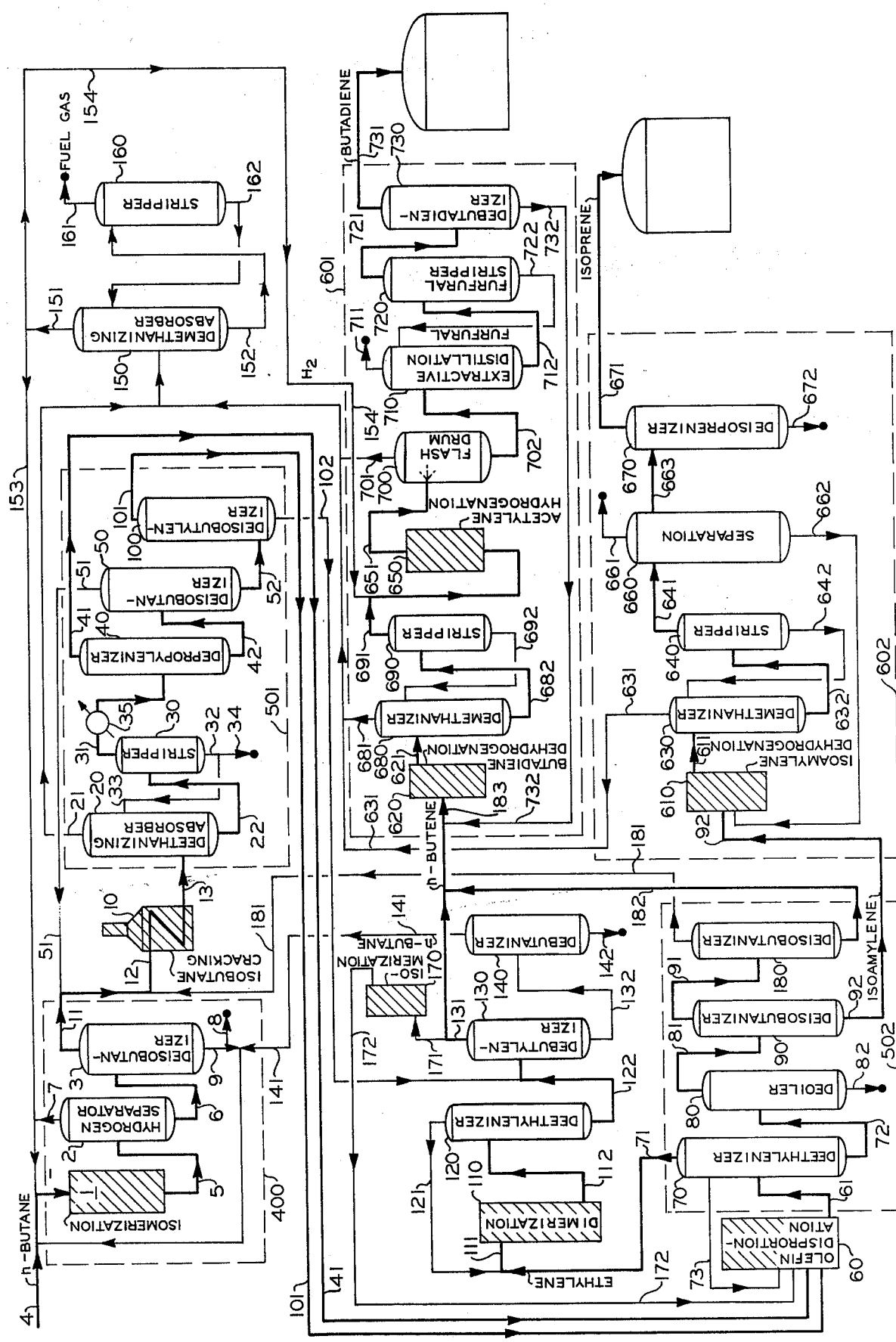

PRODUCTION OF ISOPRENE FROM ISOBUTANE

This invention relates to hydrocarbon conversion. Particularly, this invention relates to the production of isoamylene. More specifically, the present invention relates to the production of isoamylene from isobutane. In one of its even more specific aspects, this invention relates to the production of isoprene and butadiene from isobutane or n-butane.

BACKGROUND OF THE INVENTION

It is well known in the art that, e.g., propane can be cracked to produce propylene. This propylene, as is also well known, can be disproportionated to form butylenes and ethylene. The butylenes in turn can be converted to butadiene, which is a valuable monomer for rubber polymer production.

Isoamylenes are precursors for the production of isoprene, which in turn is another valuable monomer for the production of polymers. It is known that isoamylene can be produced by disproportionating isobutylene with butene-2 and/or propylene. The isopentene obtained by this disproportionation and consisting predominantly of 2-methyl butene-2 is referred to in the following as isoamylene.

In a situation where either n-butane or isobutane is available and both products cannot reasonably be converted to higher boiling hydrocarbons, such as by an alkylation process, it would be desirable to have a process available to convert the butane products into a diene, particularly into isoprene. Isoprene can be converted into various polymers in commercially developed processes.

THE INVENTION

One object of this invention is to provide a process for the production of isoamylene from isobutane.

Another object of this invention is to provide a process for the production of isoprene from isobutane or n-butane.

A further object of this invention is to provide a process for the production of both butadiene and isoprene from either isobutane or n-butane.

These and other objects, advantages, details, features and embodiments of this invention will become apparent to those skilled in the art from the following detailed description of the invention, the appended claims and the drawing, which shows a schematic flow diagram for the conversion of n-butane into isoprene and butadiene incorporating the process of the present invention.

In accordance with this invention, there is now provided a process for producing isoamylene from isobutane. In this process isobutane is first cracked to form isobutylene and propylene. These two olefins are separated from the cracked isobutane and introduced into a disproportionation zone. In this disproportionation zone, isobutylene and propylene together are converted into ethylene and isoamylene. From the effluent of the disproportionation zone, isoamylene is withdrawn.

The process of this invention has the considerable advantage of matching two main process steps, namely the cracking step and the disproportionation step. The cracking of isobutane yields isobutylene and propylene nearly in equal molar amounts. The disproportionation reaction to produce isoamylene ideally starts with feedstocks of equal molar amounts of isobutylene and propylene in accordance with the equation:

$$\text{iso } C_4H_8 + C_3H_6 \rightarrow \text{iso } C_5H_{10} + C_2H_4.$$

Thus the process of this invention is very efficient.

The further advantage of this invention resides in the fact that ethylene is produced in the disproportionation reaction which can be dimerized to butenes and the butenes can be dehydrogenated to butadiene. Thus isobutane can be efficiently converted into isoprene and butadiene.

The cracking step of the process of this invention is known in the art. Isobutane can, for instance, be thermally converted into isobutylene and propylene. Details of this thermal cracking step are described in U.S. Pat. Nos. 2,816,150 and 2,848,522. Another known process to crack isobutane is a catalytic cracking process. Such a process converting isobutane to isobutylene and propylene utilizing a catalyst is described in detail in U.S. Pat. No. 3,751,514.

The effluents from the various chemical reactions in this invention have to be separated in separation zones. All of these separation zones comprise generally several individual separating units such as fractionation towers, absorbers, strippers, etc. These units will be explained in some detail in connection with the drawing. It has to be emphasized, however, that the separation actually achieved can be achieved in various manners and the invention should not be unduly limited to the specific manner these separations are shown in the drawing.

In the disproportionation step, the basic reaction is to convert 1 mole each of isobutylene and propylene into 1 mole each of isoamylene and ethylene. This known reaction is described in detail, for instance, in the U.S. Pat. Nos. 3,590,096, and 3,723,562. The disproportionation reaction is sometimes also generically referred to as the Triolefin process, although there are generally more than three olefins involved in the process.

The conversion of isoamylene to isoprene, as well as the conversion of n-butene to butadiene, are processes known in the art. These conversions essentially involve dehydrogenation reactions, and commercial units have been used to carry out these reactions together with various separations and recycle steps. The conversion of isoamylene to isoprene is described in detail in U.S. Pat. No. 3,565,969. The conversion and dehydrogenation of n-butenes into butadiene is described in U.S. Pat. No. 2,866,790.

In accordance with this invention, two as such known processes, namely the hydrocarbon cracking process to convert saturated hydrocarbon into olefins and the disproportionation process to convert olefins into other olefins differing in the number of carbon atoms, have been matched. The isobutane cracking results in an effluent containing propylene and butylene in concentrations so that these olefins can be directly used in the triolefin or disproportionation process to produce isoamylenes. The isobutane cracking is therefore carried out under the following conditions:

| Isobutane Cracking Conditions | | |
| --- | --- | --- |
| | Range | Preferred |
| Pressure, psig | atm. – 150 | about 50 |
| Temperature, °F | 1200 – 1350 | about 1300 |

The triolefin reaction is carried out with a catalyst as disclosed in U.S. Pat. No. 3,565,969 that is hereby incorporated by reference. The reaction conditions with this catalyst are shown in the following table:

| Triolefin Reaction Conditions | | |
|---|---|---|
| (Catalyst as described in U.S. Pat. 3,565,969, particularly column 2, lines 35 ff.) | | |
| | Range | Preferred |
| Pressure, psig | 200 – 400 | about 300 |
| Temperature, °F | 750 – 850° | about 800° |

This combination or matching of the isobutane cracking with the $C_3$–$C_4$ olefin disproportionation results in an optimized production of isoamylenes from isobutane. This specific combination with the conditions listed above is thus a preferred embodiment of this invention.

Further details and preferred embodiments of this invention will become apparent to those skilled in the art from the following description of the drawing. The main product flow is shown in thick lines. Reboilers, refluxes, knock-out drums, valves, compressors, etc., have been omitted in order not to render the drawing too complicated.

The drawing shows a schematic overall flow diagram for the process of converting n-butane into isoprene and butadiene. Basically, the process comprises the following steps. In a butane isomerization zone 400, n-butane is isomerized to yield an isobutane stream. This isobutane stream is cracked in an isobutane cracking reactor 10 to yield an effluent comprising isobutene and propylene. From this effluent in a first separation zone 501, an isobutylene stream, a propylene stream, and a recycle isobutane stream are separated. The olefin streams are introduced into an olefin disproportionation zone 60 from which an ethylene and isoamylene-containing stream is separated. From this effluent from the disproportionation zone 60, isoamylene as well as ethylene are separated in a separation zone 502. The isoamylene is converted in an isoprene production zone 602 to yield isoprene. The ethylene stream is dimerized in a dimerization zone 110 to produce n-butene. The n-butene finally is converted into butadiene in a butadiene production zone 601.

The individual portions of this overall process, as well as various recycles, will be described in the following.

The butane isomerization zone 400 comprises an isomerization reactor 1 in which the n-butane feed stream is introduced via line 4. The effluent from this isomerization zone 1 is passed via line 5 to a hydrogen separator 2. Hydrogen withdrawn from this hydrogen separator 2 is passed via line 7 back into the isomerization zone. The purpose of hydrogen present in the butane isomerization zone is to prevent or reduce coke formation which occurs in the absence of hydrogen. The bottom effluent from the hydrogen separator 2 comprising isobutane, as well as unreated n-butane, is passed via line 6 to a deisobutanizer 3. From this deisobutanizer 3 a bottom stream comprising n-butane is withdrawn via line 9 and is reintroduced into the isomerization reactor 1, together with the n-butane feedstock. A certain quantity of heavy materials when present is withdrawn from the deisobutanizer 3 via line 8. The overhead effluent from the deisobutanizer 3, consisting essentially of isobutane, is passed via lines 11 and 12 as the main feedstock into the isobutane cracking zone 10. In this isobutane cracking zone, a portion of the isobutane introduced is converted into isobutylene and propylene.

The effluent from the isobutane cracking zone 10 is passed via line 13 into the first separation zone 501. This effluent is first introduced into a deethanizer absorber 20 via line 13. A gaseous overhead stream leaves this deethanizing absorber via line 21. This overhead gas stream consists essentially of hydrogen, methane, ethylene, ethane and small quantities of propylene and propane. From the deethanizing absorber a bottom stream 22 is withdrawn and introduced into stripper 30. From stripper 30 an overhead stream 31, consisting essentially of propylene, propane, isobutylene, isobutane and some n-butane, as well as some n-butylenes is introduced via line 31 into a heater 35. The bottom stream 32 comprising lean absorption oil of the stripper 30 is partially reintroduced into the deethanizing absorber 20 via line 33 as the absorbing fluid and is partially removed via line 34.

The stream leaving the heating unit 35 is introduced into a depropylenizer 40 from which an overhead stream 41 consisting essentially of propylene is withdrawn. The bottom stream from the depropylenizer 40 is passed via line 42 into a deisobutanizer 50 from which an overhead stream consisting essentially of isobutane, some propane and small quantities of isobutylene and propylene is withdrawn via line 51. The bottom stream from the deisobutanizer is passed via line 52 into a deisobutylenizer 100 from which an overhead stream consisting essentially of isobutylene, some n-butylenes and a small quantity of isobutane is withdrawn via line 101. The bottom stream withdrawn from the deisobutylenizer 100 via line 102 consists essentially of heavier materials, some n-butane and some n-butylenes. This bottom stream is passed via line 102 through a debutylenizer 130 and a debutanizer 140, as will be explained later. The overhead stream 51 withdrawn from the deisobutanizer 50 is recycled to the isobutane cracking zone 10 via this line 51. The overhead stream 21 withdrawn from the deethanizing absorber 20 is introduced into a demethanizing absorber column 150, from which an overhead stream 151 consisting essentially of hydrogen and some methane is withdrawn overhead. The bottom stream 152 withdrawn from the demethanizing absorber is introduced into a stripper 160 from which an overhead stream 161 consisting essentially of fuel gas is withdrawn, whereas the bottom stream comprising lean absorption oil 162 from this stripper 160 is reintroduced into the demethanizing absorber 150. The hydrogen in line 151 is in part introduced into the isomerization reaction zone 1 in which the n-butane is converted into isobutane via line 153 and is in part passed via line 154 to an acetylene hydrogenation zone 650 in which acetylenes, unavoidably produced during the butadiene production, are hydrogenated.

The propylene in line 41, as well as the isobutylene in line 101, are passed into an olefin disproportionation zone 60. In this olefin disproportionation zone, these olefins are partially disproportionated into isoamylene and ethylene. The effluent from the disproportionation zone 60 is passed via line 61 into a second separation zone 502. First the effluent in line 61 is passed into a deethylenizer 70 from which an overhead stream 71 consisting essentially of ethylene is withdrawn. Via line 73 a side stream comprising unreacted olefins is recycled from the deethylenizer 70 to the olefin disproportionation zone 60. The bottom stream from the deethylenizer 70 is passed via line 72 to a deoiler 80. From this deoiler 80, a residue of high-boiling components is removed at 82, and an overhead stream 81 is passed into a deisobutanizer 90 from which a bottom stream 92, consisting essentially of isoamylene, is withdrawn and passed to an isoprene production unit 602. An overhead stream from the deisobutanizer is passed via line 91 to another deisobutanizer 180 from which an overhead stream consisting essentially of isobutane is withdrawn via line 181. A bottom stream consisting essentially of n-butene is withdrawn from the deisobutanizer 180 via line 182.

The overhead stream 171 from the deethylenizer consisting essentially of ethylene is passed via line 111 to an ethylene dimerization zone 110. The effluent of this ethylene dimerization zone 110 is passed via line 112 to a deethylenizing column 120 from which an overhead stream consisting essentially of ethylene is withdrawn via line 121. The bottom effluent from the deethylenizer is passed via line 122 to a debutylenizer 130 from which an overhead stream 131 consisting essentially of n-butylene is withdrawn via line 131. The bottom stream from the debutylenizer 130 is passed via line 132 to a debutanizer from which an overhead stream consisting essentially of n-butane is withdrawn via line 141. A bottom stream consisting of heavier hydrocarbons is withdrawn from the debutanizer 140 via line 142.

The overhead stream from the deethylenizer 120 is passed via line 121 back into the dimerization zone 110. The butylene overhead stream 131 from the debutylenizer 130 is in part introduced into an isomerization zone 170 via line 171. From this isomerization zone 170, an effluent comprising mainly n-butene-2 is withdrawn via line 172 and reintroduced into the olefin disproportionation reaction zone 60. This n-butylene-2 reacts with one molecule of propylene in accordance with the equation:

$$n - C_4H_8 + iso\ C_4H_8 \rightarrow iso\ C_5H_{10} + C_3H_6.$$

Thus by properly controlling the quantity of n-butene-2 introduced via line 172 into the olefin disproportionation reaction zone 60, an eventual surplus of isobutylene over the propylene introduced into this zone can be compensated for. The rest of the n-butene from the overhead stream 131 is passed together with the n-butene from line 182 via line 183 to the production of butadiene in unit 601.

The overhead effluent in line 141 consisting essentially of n-butane is reintroduced, together with the bottom effluent from the deisobutanizer 3, into the isomerization reactor 1. Similarly, the overhead effluent consisting essentially of isobutane in line 181 from the deisobutanizer 180 is reintroduced into the isobutane cracking zone 10 via line 12.

The isoamylene in stream 92 is converted into isoprene in unit 602. The isoamylene stream is first passed into an oxidative dehydrogenation reactor 610. Steam is also introduced into the reactor 610. The effluent from this oxidative dehydrogenation reactor is passed via line 611 to a demethanizer 630. The overhead stream leaving the demethanizer and containing hydrogen is passed via line 631 to the demethanizing absorber 150. The bottom stream from the demethanizer 630 is passed via line 632 to a stripper 640 from which the overhead stream is passed via line 641 to a separator 660. This separator actually comprises two extractive distillation steps but is shown in the drawing just as one unit. The bottom stream from the stripper 640 is passed back to the demethanizer via line 642 as lean absorption oil. From the separator 660 an overhead stream comprising some paraffins leaves via line 661. A product stream comprising predominantly isoprene leaves via line 663 and a bottom stream comprising isoamylene leaves via line 662 and is reintroduced into the dehydrogenation reactor 610. The stream in line 663 is finally separated in the deisopropenizer 670 to yeild an overhead stream of isoprene in line 671 and a bottom stream in line 672.

Similarly to the conversion of the main isoamylene stream into isoprene, the n-butene side stream in line 183 is converted into butadiene in zone 601 by passing the n-butene stream into a dehydrogenation reactor 620 in which part of the n-butylene is converted into butadiene. Steam is also passed into the reactor 620. The effluent from the dehydrogenation reactor 620 is passed via line 621 to a demethanizing absorber 680 from which overhead gas stream comprising hydrogen is withdrawn via line 681 and passed to the demethanizing absorber 150. The bottom stream from demethanizer 680 is passed via line 682 to stripper 690 from which the bottom stream is reintroduced via line 692 into the absorber 680. The overhead stream is passed via line 691 from the stripper 690 through an acetylene hydrogenation unit 650. In this unit 650 the acetylenes are hydrogenated with hydrogen introduced from the absorber 150 via line 154. From the hydrogenation unit the effluent is passed via line 651 to a flash drum 700. The gaseous effluent from the flash drum 700 is passed via line 701 to the absorber 150, whereas the liquid bottom effluent is passed via line 702 from the flash drum into an extractive distillation column 710. Overhead paraffins comprising stream is withdrawn from this column 710 via line 711. The bottom stream from the column 710 is withdrawn via line 712 and introduced into a furfural stripper 720. The lean furfural comprising bottom stream is reintroduced into the extractive distillation column 710 via line 722. The overhead stream comprising butadiene and n-butene-2 is passed via line 721 from the stripper 720 to a debutadienizer 730 from which substantially pure butadiene is withdrawn overhead via line 731 whereas a butene-2 comprising stream is withdrawn via line 732 and reintroduced into the dehydrogenation reactor 620.

The central and main portion of this overall reaction for the production of isoprene is the process converting isobutane into isoamylene. If no isobutane as such is available but n-butane is available, the isobutane is first produced by isomerization of the n-butane into isobutane.

The following calculated example is given to further illustrate the invention and is not intended to limit the scope thereof. This example shows a calculated material balance for the conversion of isobutane into isoamylene. The numerals of the various streams shown in the following table refer to the reference numerals of the corresponding stream in the drawing. The calculated example is based on a feed of 3,000 barrels of isobutane per day.

| | ISOAMYLENE PRODUCTION (Figures in lbs./day) | | | | | | | | | | | | |
|---|---|---|---|---|---|---|---|---|---|---|---|---|---|
| Stream No. | 11 | 51 | 12 | 13 | 21 | 31 | 34 | 41 | 42 | 51 | 52 | 101 | 102 | 172 |
| Component | | | | | | | | | | | | | | |
| Hydrogen | | | | 270 | 270 | | | | | | | | | |

-continued

| | ISOAMYLENE PRODUCTION (Figures in lbs./day) | | | | | | | | | | | | |
|---|---|---|---|---|---|---|---|---|---|---|---|---|---|
| Methane | | | | 4,051 | 4,051 | | | | | | | | |
| Ethylene | | | | 1,208 | 1,208 | | | | | | | | |
| Ethane | | | | 477 | 477 | | | | | | | | |
| Propylene | | 351 | 351 | 7,923 | 371 | 7,552 | | 7,201 | 351 | 351 | | | | |
| Propane | | 1,058 | 1,058 | 1,108 | 50 | 1,058 | | | 1,058 | 1,058 | | | | |
| Isobutylene | | 700 | 700 | 11,922 | | 11,922 | | | 11,922 | 700 | 11,222 | 11,222 | | |
| n-Butylenes | | | | 127 | | 127 | | | 127 | | 127 | 60 | 67 | 853 |
| Isobutane | 24,600 | 16,000 | 40,600 | 16,240 | | 16,240 | | | 16,240 | 16,000 | 240 | 240 | | |
| n-Butane | 1,295 | | 1,295 | 136 | | 136 | | | 136 | | 136 | | 136 | |
| Isoamylenes | | | | | | | | | | | | | | |
| Heavies | | | | 542 | | 142 | 400 | | 2 142 | | 142 | | 142 | |
| Total | 25,895 | 18,109 | 44,004 | 44,004 | 6,427 | 37.177 | 400 | 7,201 | 29,976 | 18,109 | 11,867 | 11,522 | 345 | 853 |
| Stream No. | 91 | 96 | 87 | 61 | 72 | 73 | 71 | 82 | 81 | 144 | 181 | 131 | 92 | |
| Component | | | | | | | | | | | | | | |
| Hydrogen | | | | | | | | | | | | | | |
| Methane | | | | | | | | | | | | | | |
| Ethylene | | | | 5,216 | | | 5,216 | | | | | | | |
| Ethane | | | | | | | | | | | | | | |
| Propylene | | | 18,597 | 11,396 | | 11,396 | | | | | | | | |
| Propane | | | | | | | | | | | | | | |
| Isobutylene | | | 26,717 | 15,495 | | 15,495 | | | | | | | | |
| n-Butylenes | 100 | 100 | 2,135 | 1,222 | 100 | 1,122 | | | 100 | 100 | | 5,000 | | |
| Isobutane | 240 | 240 | 5,040 | 4,800 | 240 | 4,560 | | | 240 | | 240 | | | |
| n-Butane | | | | | | | | | | | | | | |
| Isoamylenes | | | | 14,280 | 14,280 | | | | 14,280 | | | | 14,280 | |
| Heavies | | | 70 | 150 | 150 | | | 150 | | | | | | |
| Total | 340 | 340 | 52,559 | 52,559 | 14,770 | 32,573 | 5,216 | 150 | 14,620 | 100 | 240 | 5,000 | 14,280 | |

Reasonable variations and modications, which will become apparent to those skilled in the art, can be made in this invention without departing from the spirit and scope thereof.

I claim:

1. A process for producing isoprene comprising
   a. introducing isobutane into a cracking zone and cracking isobutane in said cracking zone,
   b. withdrawing a cracked effluent comprising isobutylene, propylene and isobutane from said cracking zone,
   c. introducing said cracked effluent into a first separation zone,
   d. withdrawing a propylene stream and an isobutylene stream from said first separation zone,
   e. introducing said propylene stream and said isobutylene stream into a disproportionation zone and disproportionating said streams in said disproportionation zone to form isoamylene,
   f. withdrawing an effluent from said disproportionation zone,
   g. introducing said disproportionated effluent into a second separation zone,
   h. withdrawing an ethylene-comprising stream from said second separation zone,
   i. passing said ethylene-comprising stream to a dimerization zone and converting ethylene of said ethylene-comprising stream to butylenes,
   j. introducing at least a portion of said butylenes into an isomerization zone in which 1-butylene is isomerized into 2-butylene and wherein at least a portion of the butylenes from said isomerization zone are introduced into said disproportiontion zone,
   k. withdrawing an isoamylene-comprising stream from said second separation zone, and
   l. dehydrogenating isoamylene from said isoamylene-comprising stream in a first dehydrogenation zone to produce isoprene.

2. A process in accordance with claim 1 wherein at least a portion of said butylenes of said butylenes-comprising stream is introduced into a second dehydrogenation zone to convert butylenes into butadiene and wherein butadiene is withdrawn from the effluent from said second dehydrogenation zone as the second product of the process.

3. A process in accordance with claim 1 wherein said first separation zone comprises a deethanizer, a depropylenizer, a deisobutanizer, a deisopropylenizer and, wherein said cracked effluent is introduced into said deethanizer from which a first overhead effluent comprising ethane and lighter gases and a first bottom effluent are withdrawn, wherein at least a portion of said first bottom effluent is introduced into said depropylenizer from which a second overhead stream comprising propylene and a second bottom stream comprising isobutane, isobutylene and heavies are withdrawn, wherein said second bottom stream is introduced into a deisobutanizer from which a third overhead stream comprising isobutane, and a third bottom stream comprising isobutylene and heavies are withdrawn, wherein said third bottom stream is introduced into said deisobutylenizer from which a fourth overhead stream comprising isobutylene and a fourth bottom stream comprising heavies are withdrawn, wherein said second overhead stream comprising propylene and said fourth overhead stream comprising isobutylene are introduced into said disproportionation zone, and wherein said third overhead stream comprising isobutane is introduced into said cracking zone.

4. A process in accordance with claim 1 wherein said second separation zone comprises a first deethylenizer, a first deisobutanizer, and a second deisobutanizer, wherein said disproportionated effluent is introduced into said first deethylenizer, wherein an overhead effluent stream is withdrawn from said first deethylenizer and is introduced into a dimerization zone, wherein a bottom stream withdrawn from said first deethylenizer is passed via a deoiler into said first deisobutanizer from which an overhead stream comprising isobutane and n-butylene and a bottom stream consisting essentially of isoamylene are withdrawn, wherein the overhead stream from said first deisobutanizer is introduced into said second deisobutanizer from which a bottom stream comprising butylenes is withdrawn and an overhead stream comprising isobutane is withdrawn and introduced into said cracking zone, wherein the effluent from said dimerization zone is introduced into a second deethylenizer from which an ethylene-comprising stream is withdrawn overhead and reintroduced into said dimerization zone and from which a bottom stream comprising n-butene and n-butane is withdrawn and passed into a debutylenizer from which an n-butene-comprising stream is withdrawn overhead and an n-butane-comprising stream is withdrawn from the bottom, wherein said n-butene-comprising stream leaving the debutylenizer, as well as said bottom stream comprising butylene leaving said second deisobutanizer are introduced into a second dehydrogenation zone from which a butadiene-comprising effluent is withdrawn and wherein butadiene is separated from said butadiene-comprising effluent.

5. A process in accordance with claim 1 wherein said isobutane stream is produced by introducing an n-butane stream into an isomerization reaction zone, passing the effluent from said isomerization reaction zone into a third separation zone and removing an isobutane-comprising stream from said third separation zone.

* * * * *